United States Patent [19]

Mackool

[11] Patent Number: 5,685,841
[45] Date of Patent: Nov. 11, 1997

[54] SUPPORT FOR FLUID INFUSION TUBE FOR USE DURING EYE SURGERY

[76] Inventor: Richard J. Mackool, c/o The Mackool Family Partnership 31-27 41st St., Astoria, N.Y. 11103

[21] Appl. No.: 514,555

[22] Filed: Aug. 14, 1995

[51] Int. Cl.⁶ .................................................. A61B 17/20
[52] U.S. Cl. .................................................. 604/22; 604/35
[58] Field of Search .................... 604/22, 27, 30, 604/36, 138, 264, 280, 282, 35; 138/172–174

[56] References Cited

U.S. PATENT DOCUMENTS

| | | | |
|---|---|---|---|
| 3,902,495 | 9/1975 | Weiss et al. | 128/276 |
| 4,369,785 | 1/1983 | Rehopf et al. | 604/35 |
| 4,573,979 | 3/1986 | Blake | 604/240 |
| 5,069,674 | 12/1991 | Fearnot et al. | 604/282 |
| 5,176,660 | 1/1993 | Truckai | 604/282 |
| 5,190,520 | 3/1993 | Fenton, Jr. et al. | 604/43 |
| 5,334,169 | 8/1994 | Brown et al. | 604/282 |
| 5,380,304 | 1/1995 | Parker | 604/282 |
| 5,562,612 | 10/1996 | Fox | 604/27 |

FOREIGN PATENT DOCUMENTS

| | | | |
|---|---|---|---|
| 2918282 | 11/1980 | Germany | 604/282 |
| 4137132 | 5/1993 | Germany | 604/282 |
| 3051057 | 3/1991 | Japan | 604/282 |
| 405084302 | 4/1993 | Japan | 604/264 |
| 406142207 | 5/1994 | Japan | 604/264 |
| 2017182 | 10/1979 | United Kingdom | 604/280 |

*Primary Examiner*—Corrine M. McDermott
*Assistant Examiner*—Deborah B. Blyveis
*Attorney, Agent, or Firm*—Cobrin Gittes & Samuel

[57] ABSTRACT

A support for reinforcing a fluid infusion tube to prevent it from kinking during a surgical operation. The support runs to the distal end of the tube and is either embedded in the wall of the tube, adhered or heat sealed to the tube either on the tube's interior surface or on the exterior surface, or loosely retained within the lumen. The support may be coiled about the exterior or interior of the tube to provide the desired rigidity to prevent kinking.

20 Claims, 3 Drawing Sheets

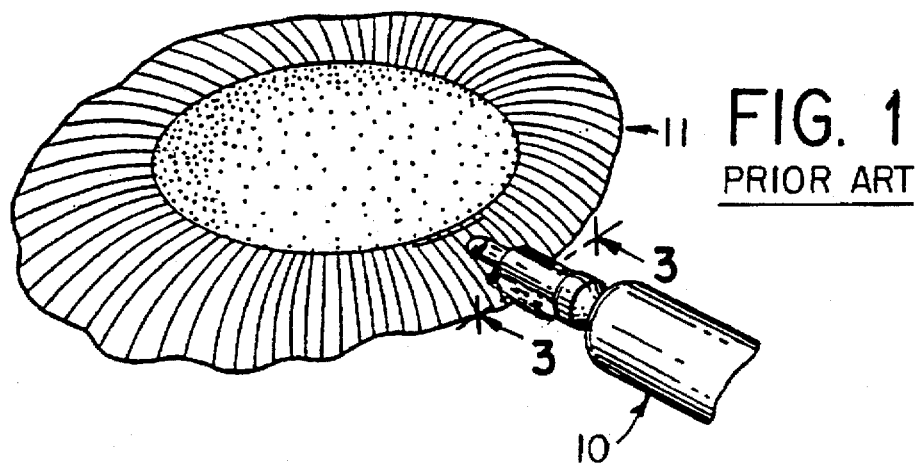
FIG. 1
PRIOR ART
FIG. 2
PRIOR ART
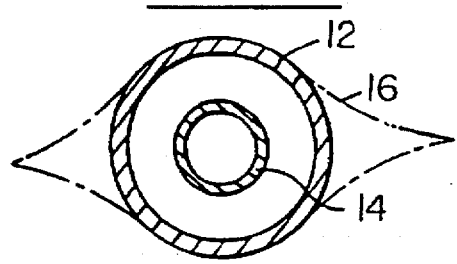
FIG. 3
PRIOR ART
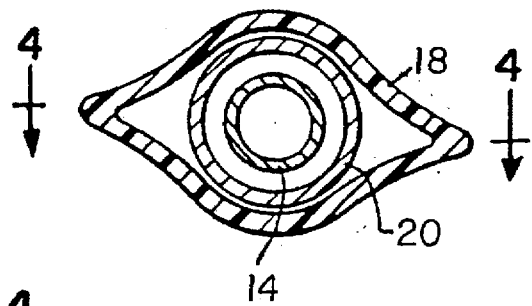
FIG. 4
PRIOR ART
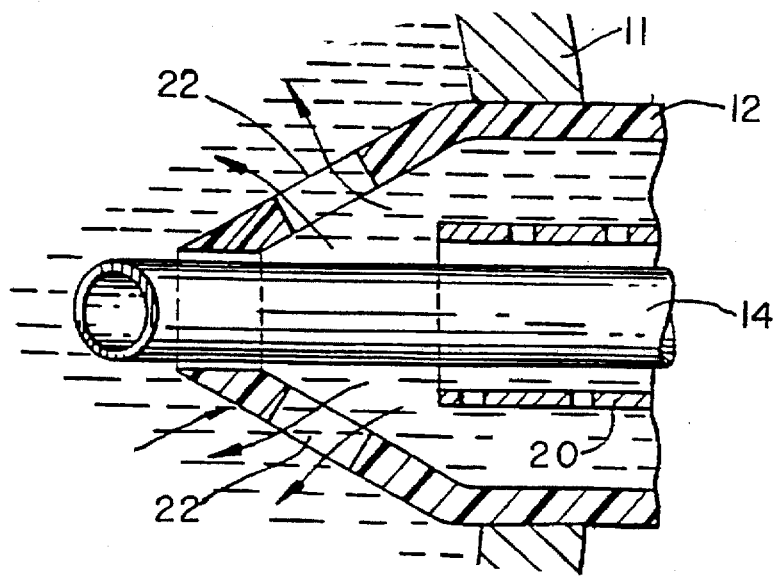

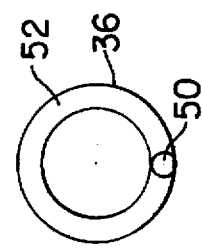
FIG. 10
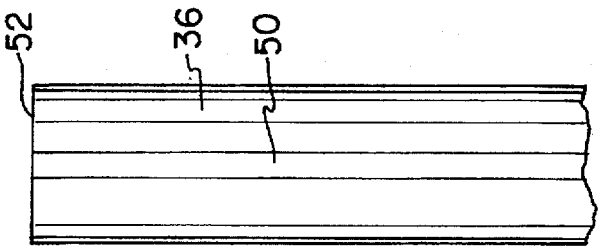
FIG. 11
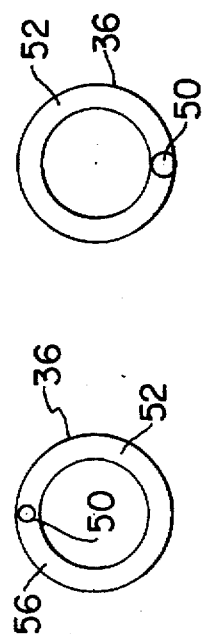
FIG. 8
FIG. 9
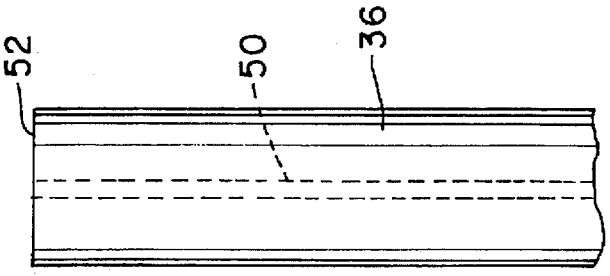
FIG. 6
FIG. 7
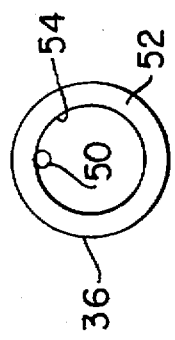
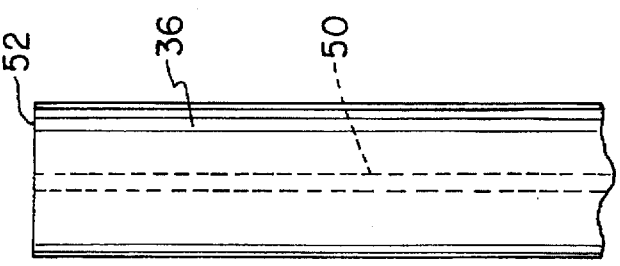
FIG. 5
PRIOR ART
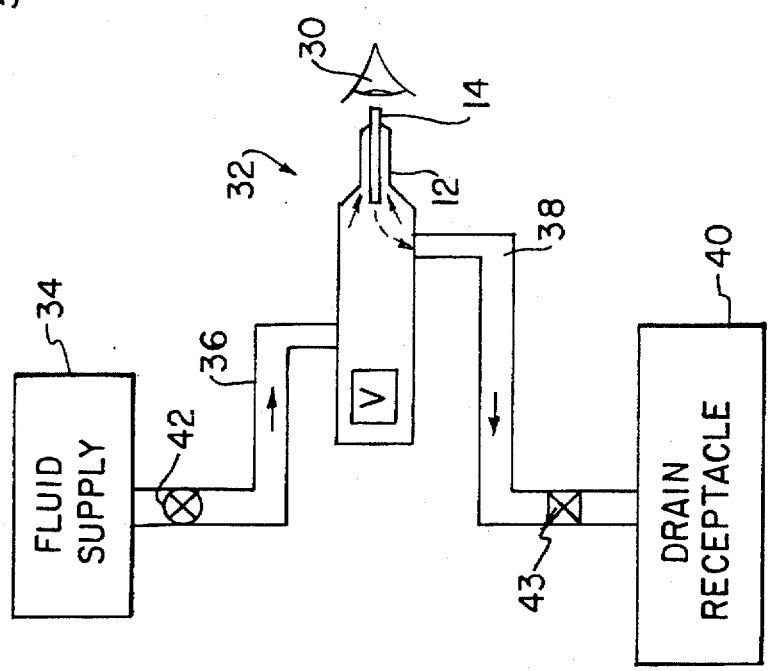

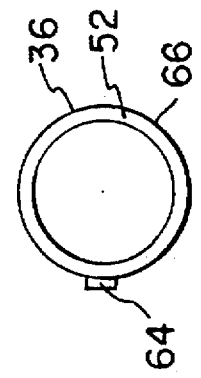
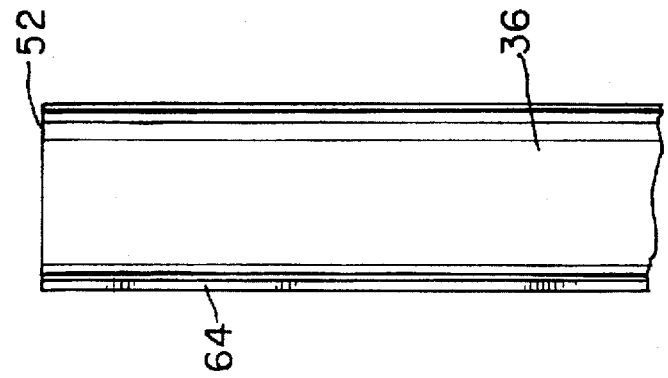
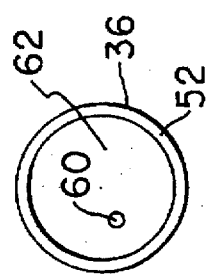
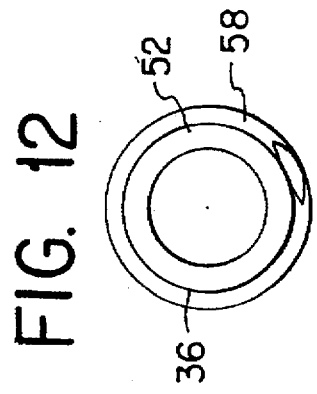
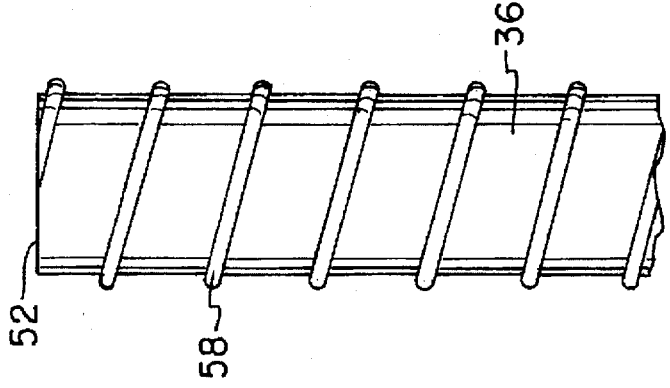

SUPPORT FOR FLUID INFUSION TUBE FOR USE DURING EYE SURGERY

BACKGROUND OF THE INVENTION

This invention relates generally to a support for a tube that conveys fluid to or from a surgical instrument, such as an ultrasonic or an irrigating/aspiration handpiece for use in eye surgery, such as cataract eye surgery.

A wide array of fluid-irrigated, ultrasonically-operated cutting devices have been developed for ophthalmological surgical techniques such as phacoemulsification—a method for removing a cataract through a surgical incision in the eye.

Heretofore, phacoemulsification involved the use of a dual chambered handpiece consisting of a hollow metallic needle surrounded by a tubular sleeve. The needle is vibrated ultrasonically at selected frequencies and amplitudes to fracture the cataract to be removed and replaced by an intraocular lens. The fractured cataract tissue is aspirated through the needle interior through the use of a suction force. A fluid is infused into the eye through the tubular sleeve to irrigate the eye. The tubular sleeve has been made heretofore preferably of a soft material such as silicone or less desirably of a rigid composition such as metal or teflon.

U.S. Pat. No. 5,084,009 ('009 patent), entitled FLUID INFUSION SLEEVE FOR USE DURING EYE SURGERY to Richard Mackool on Jan. 28, 1992, whose contents are incorporated herein by reference, discloses such a silicone sleeve and discusses the problems that arise from the incision compressing the non-rigid, pliable silicone sleeve. Such problems include the sleeve collapsing on the vibrating needle so that the needle, which is being vibrated at ultrahigh frequencies, rubs against the sleeve and the irrigation flow path between the needle and the sleeve becoming constricted due to the collapsed sleeve.

The sleeve through which irrigation takes place, i.e., delivering fluid to the eye, should be made of soft material that can deform to match the contour of the eye incision and thereby prevent leakage. To prevent the sleeve from collapsing on the vibrating needle, the '009 patent suggests surrounding the needle with a rigid sleeve that is interposed between the needle and the outer, soft, silicone sleeve. Thus, a collapse of the outer, soft, silicone sleeve will be onto the metallic sleeve rather than in rubbing contact with the vibrating needle.

The experience of the applicant, who has performed literally thousands of cataract eye operations, has found that during the course of an eye surgical operation, the tubes that lead to the handpiece of the phacoemulsification instrument from a surgical console are susceptible to unintentional kinking by medical personnel if the tubes are made from soft, pliable material that may elastically expand under pressure. These tubes include the infusion tube from the fluid supply to the handpiece and the discharge tube from the handpiece to the drainage receptacle or suction. There is no vibratory needle within these tubes so there is no risk of making unwanted rubbing contact as would prompt the solution of interposing a metallic sleeve to surround the needle as taught in the '009 patent.

Kinking may lead to severe consequences. If the infusion tube becomes kinked, a pressure loss downstream may lead to deflation of the eye. Such deflation could lead to collapse of certain eye tissues upon each other or upon the surgical instrument which extends into the eye. Either way, the tissues which are most likely to be damaged from such deflation are the cornea, the iris and the lens capsule, all surrounding the cataract. Fragile cells which line the inside of the cornea are known as corneal endothelium and they cannot be regenerated by the eye. Damage to the corneal endothelium can cause permanent damage to the cornea, resulting in a corneal clouding and decreased vision. A corneal transplant may then be necessary.

If the discharge tube becomes inadvertently kinked or, as commonly occurs, blocked by fractured tissue, the eye will still be pressurized, but the surgical operation will cease until the kink or blockage is eliminated. At the time of the kinking or blocking, however, the pressure falls downstream so that upon removal of the kink or blockage, a sudden surge in the outflow rate arises as the downstream vacuum acts to drain the eye due to loss of upstream pressure. This sudden drop in upstream pressure is felt by the eye, tending to create some deflation until normal flow is restored. It would be desirable to avoid such deflation by allowing the infusion tube to expand to hold more fluid and develop elastic energy which upon release can cause increase of flow into the eye and thereby counter the abrupt surge in the outflow upon removal of the kink or blockage. Soft material, such as silicone, elastically expands under pressure build-up and so its use is preferable.

Upon release of the blockage or kinking, the expanded, soft infusion tube contracts back to its unexpanded state and thereby provides a temporarily greater volume of fluid flow per second than was being supplied to the eye before the kinking or blocking arose. Thus, the volumetric loss of fluid during the sudden surge in outflow upon removal of the kink or blockage is better compensated by the larger volume of fluid readily available under pressure in the expanded, soft infusion tube.

It would therefore be desirable to modify the infusion tube to avoid kinking and yet allow the infusion tube to be made of soft, pliable material that is elastically expandable. Although the discharge tube if made from the same material, could be also modified in the same manner, it is usually preferable to use rigid material for the discharge tube. This tends to reduce the extent of the previously described surge upon removal of blockages and would reduce the possibility of kinking.

Tube kinking is also a problem for tubes connected with handpieces used during performance of other medical procedures other than eye surgery, such as in orthopedic and cardiovascular surgical procedures. It would be desirable to prevent flow blockage from tube kinking for these other medical procedures as well.

SUMMARY OF THE INVENTION

The present invention relates to a reinforcement that prevents an infusion tube from kinking where the tube is made from a soft, pliable material that is elastically expandable. The reinforcement may lie within the wall of the tube, be external of the tube and extend to the distal end of the tube, or be contained within the lumen of the tube itself. If external, the reinforcement may be in the form of a coil wrapping around the tube to its distal end. The reinforcement may be in the form of a single rigid strip that is either fastened to the wall of the tube or embedded in it. However, the soft, pliant nature of the tube should not be compromised.

BRIEF DESCRIPTION OF THE DRAWINGS

For a better understanding of the present invention, reference is made to the following description and accompanying drawings, while the scope of the invention is set forth in the appended claims.

FIG. 1 shows a conventional phacoemulsification handpiece whose tip is being inserted into an eye;

FIG. 2 shows a cross-section of a conventional phacoemulsification tip of the type of FIG. 1 along section line 3—3 if the infusion tube of FIG. 1 were cylindrical. The incision cut is represented in outline with dash-dot lines;

FIG. 3 shows a cross-section taken across section line 3—3 of FIG. 1;

FIG. 4 shows a cross-section taken across section line 4—4 of FIG. 3;

FIG. 5 shows an schematic representation of a conventional set-up that employs the phacoemulsification instrument of FIGS. 1 or 2;

FIG. 6 is an end view of a tube with support in accordance with a first embodiment of the invention.

FIG. 7 is a longitudinal view thereof.

FIG. 8 is an end view of a tube with support in accordance with a second embodiment of the invention.

FIG. 9 is a longitudinal view thereof.

FIG. 10 is an end view of a tube with support in accordance with a third embodiment of the invention.

FIG. 11 is a longitudinal view thereof.

FIG. 12 is an end view of a tube with support in accordance with a fourth embodiment of the invention.

FIG. 13 is a longitudinal view thereof.

FIG. 14 is an end view of a tube with support in accordance with a fifth embodiment of the invention.

FIG. 15 is a longitudinal view thereof.

FIG. 16 is an end view of a tube with support in accordance with a sixth embodiment of the invention.

FIG. 17 is a longitudinal view thereof.

DESCRIPTION OF THE PREFERRED EMBODIMENT

FIG. 1 shows a conventional phacoemulsification instrument 10 being inserted into an eye 11 containing a cataract which is to be removed. The vibrating hollow needle includes a cataract fracturing tip as is known. FIG. 2 shows an infusion sleeve 12 which is circular in cross-section and is concentric with the vibrating hollow needle 14. Normally, infusion fluid is infused into the eye through sleeve 12 and is aspirated from the eye together with the fractured cataract through the interior of the vibrating hollow needle 14.

As can be seen in FIG. 2, infusion sleeve 12 is circular in cross-section and shown in phantom lines is the ellipsoidal shape 16 of the wound incision caused by the insertion of a conventional phacoemulsification instrument in the eye of the person who is being operated upon. Thus, gaps exist that are not filled by the infusion sleeve 12.

To rectify this situation, FIG. 3 shows a conventional phacoemulsification instrument in FIG. 3 from the teaching of U.S. Pat. No. 5,084,009 whose infusion sleeve 18 is of a ellipsoidal cross-section. As a consequence of the ellipsoidal shape, there is no wound leakage, pressure in the eye is maintained and the problems associated with wound leakage are avoided. In addition, the infusion sleeve 18 is made of a soft, pliable material. A rigid, noncompressible sleeve 20 is surrounded by this infusion sleeve 18 and acts as a barrier between the infusion sleeve 18 and the needle 14 in the event the infusion sleeve collapses, thereby preventing undesirable rubbing contact.

FIG. 4 shows the conventional use of the surgical instrument of FIGS. 1 and 3. Here, the concentric relationship between the needle 14, the rigid, noncompressible sleeve 20 and the infusion sleeve 18 is shown with the forward end of the infusion sleeve tapered. Ports 22 are provided in this tapered portion.

FIG. 5 shows a conventional set-up for irrigating fluid into the eye and aspirating fluid and tissue from the eye 30 continuously throughout an eye surgery operation. A conventional handpiece 32 is shown, which is constructed in any conventional manner such as that of the conventional phacoemulsification handpiece 10 of FIG. 1. There is a vibratory drive V for vibrating the hollow needle 14. An infusion sleeve 12 is provided that defines a chamber between its inner wall and the outside of the vibrating hollow needle 14. As indicated by the flow arrows, irrigation into the eye is provided normally through this chamber and aspiration from the eye is through the needle 14. The internal construction of the handpiece, such as seals and connecting linkage with the vibratory drive V have been omitted for the sake of brevity and further since such is conventional.

The irrigation is provided from a gravity fed fluid supply 34 and through an infusion tube 36 to the handpiece 32. Aspiration is provided through a discharge tube 38 from the handpiece 32 to a drain receptacle 40. In a known manner, a gate valve 42 is provided to permit flow through the infusion tube to occur. The fluid supply 34 is at a higher elevation than the eye 30. A pumping mechanism 43 is present and, when activated, suctions fluid from the eye 30 and through discharge tube 38.

The tubes 36, 38 may be susceptible to unintentional kinking by medical personnel unless they are made from an incompressible material. If the kinking arises in the discharge tube 38, the procedure stops but the eye remains inflated under pressure. If the kinking arises in the infusion tube 36, however, a pressure drop in the eye ensues that leads to its collapse. Such a collapse causes unwanted contact of eye tissue.

It may be desirable to form at least the infusion tube 36 of a soft, elastic, expandable material such as silicone to counteract the momentary flow surge that eventually results if the outflow through the discharge tube 38 becomes blocked, e.g., by tissue fragments. When such blockage arises, pressure decreases downstream to the blockage so that when the blockage is removed, there is a momentary surge in the outflow. Such a sudden event release tends to deflate the eye. To counter this deflation, the infusion tube 36 could be made to expand under a build-up of pressure, as takes place during blockage of the outflow through the discharge tube 38. When the blockage is removed, the infusion tube 36 would elastically compress back to its unexpanded state and thereby offset the momentary surge in the outflow.

The present invention, therefore, is directed at preventing kinking in the infusion tube 36 where the tube is constructed of a soft, elastic and expandable material such as silicone. This is done through reinforcement of the infusion tube itself as provided by a support running along the length of the tube.

FIGS. 6–7 show a support in the form of a rod 50 extending to the distal end 52 of the tube 36 and adhered to the interior surface 54 of the tube 36. FIGS. 8–9 show a support in the form of a rod 50 embedded within the wall 56 of the tube 36 and extending to the distal end 52 of the tube 36. FIGS. 10–11 show a support in the form of a rod 50. The tube 36 is split longitudinally to form a slit and the rod 50 is fitted in the slat to close the slat by being heat sealed to the tube 36 in a leak tight manner. The rod 50 extends to the distal end 52 of the tube. FIGS. 12–13 show a support in the form of a coil 58 adhered to the external surface of the tube 36 and running to the distal end of the tube 36. As an alternative, the coal 58 could be fitted over the tube 36 without affixing it since it will not fall off the tube 36. FIGS. 14–15 show the support in the form of a ware 60 that is loose within the lumen 62 of the tube 36. FIGS. 16–17 show a support in the form of a rod 64 adhered to the exterior surface 66 of the tube 36 and running to the distal end 52 of the tube 36.

The wire, rod or coil is made of a noncompressible material, preferably rigid, such as metal or teflon. The material of the remainder of the tube, apart from the rod or coil, is made of a soft, elastic material such as silicone or a silicone-like material. The rod, wire or coil, therefore, is less soft and pliable than the tube. The cross-sectional shape of the rod, wire or coil may be any geometric shape, such as circular, rectangular, convexly curved, concavely curved, triangular, etc.

While using an adhesive is one way to keep the tube and support together where the support is external of the tube, no adhesive is necessary where the support is embedded in the wall of the tube, confined within the lumen of the tube, or coiled about the exterior of the tube. Other conventional ways of securing the support to the tube wall other than with an adhesive may be used. For instance, the support and tube could be heat sealed together or integrally formed together.

The wire 60, rod 50, 64 or coil 58 of the present invention provides rigidity along the infusion tube 36 to prevent it from collapsing due to kinking. The wire, rod or coil may run the entire length of the infusion tube, or only a portion of the full length and need not run all the way to the distal end 52. Preferably, the outside diameter or cross-section of the wire, rod or coil is smaller than the interior diameter of the infusion tube.

In accordance with each of the embodiments of the invention, the soft, elastic material of the infusion tube 36 is reinforced by the support, preferably in the form of a single rigid strip sufficient to prevent kinking, but does not adversely compromise the pliability of the wall of the infusion tube. In addition, the support may be bendable to permit the tube 36 to bend where necessary between the handpiece 32 and the fluid supply 34. The support may be provided in the discharge tube 38 in the same manner as described with respect to the infusion tube 36.

While the preferred embodiment has application to ophthalmological surgical techniques such as phacoemulsification, handpieces are utilized in the performance of other surgical operations, such as orthopedic and cardiovascular surgery and the invention has application to those handpieces as well to prevent kinking of the infusion tube or discharge tube.

While the foregoing description and drawings represent the preferred embodiments of the present invention, it will be understood that various changes and modifications may be made without departing from the spirit and scope of the present invention.

What is claimed is:

1. A fluid conveying device that resists kinking, comprising:

an elongated tube that is compressible and pliable and which has a lumen;

a handpiece with an interior containing an aspiration needle and a sleeve defining an irrigation channel between the needle and the sleeve, said elongated tube extending exteriorly of said handpiece and being connected to said handpiece in operative fluid communication with said interior so that fluid flows between the lumen of said tube and said interior of said handpiece; and a support reinforcing said tube, said support extending in a direction of elongation of said tube and being rigid to resist kinking of said tube and thereby being less compressible and pliable than said tube.

2. A device as in claim 1, further comprising an adhesive material adhering said support to said tube.

3. A device as in claim 2, wherein said adhesive material is between an exterior of said support and an interior of said tube.

4. A device as in claim 2, wherein said adhesive is between an exterior of said tube and an exterior of said support.

5. A device as in claim 1, wherein said support is heat sealed to said tube.

6. A device as in claim 1, wherein said support is embedded within a wall of said tube.

7. A device as in claim 1, wherein said tube is split longitudinally to define a slit, said support closing said slit.

8. A device as in claim 1, wherein said support coils about an exterior of said tube.

9. A device as in claim 1, wherein said support is arranged within said lumen of said tube.

10. A device as in claim 9, wherein said support is loose within said lumen and free of adherence to said tube.

11. A device as in claim 1, wherein said support is a rigid strip.

12. A method of preventing inadvertent kinking, comprising the steps of:

conveying fluid through an elongated tube to an interior of a handpiece having irrigation and aspiration channels within said interior, the tube being connected to and in fluid communication with said interior of the handpiece; and reinforcing said tube with a support to prevent kinking of said tube, said tube being compressible and pliable, said support being rigid to resist the kinking of said tube and thereby being less compressible and pliable than said tube, said support extending in a direction of elongation of said tube.

13. A method as in claim 12, wherein said irrigation channel is defined by a hollow needle, further comprising the step of vibrating the hollow needle within the handpiece and channeling the fluid exteriorly of said hollow needle and interiorly of said hollow needle such that the fluid travels within said hollow needle in a direction opposite to that traveled by the fluid exteriorly of said hollow needle, the step of conveying including channeling the fluid to flow exteriorly of said hollow needle before the fluid flows interiorly of said hollow needle.

14. A flow apparatus that prevents inadvertent kinking during eye surgery, comprising:

an elongated tube;

a phacoemulsification handpiece connected to and in operative fluid communication with said tube for the conveyance of fluid between said tube and said phacoemulsification handpiece; and a support that reinforces said tube to prevent kinking of said tube, said tube being compressible and pliable, said support being rigid to resist kinking of said tube and thereby being less compressible and pliable than said tube and extending in a direction of elongation of said tube.

15. An apparatus as in claim 14, further comprising a vibratory hollow needle within the phacoemulsification handpiece; and a channel arranged exteriorly of said hollow needle within said handpiece, said tube being in fluid communication with said channel so that the fluid flows from said tube and into said channel before flowing within said vibrating hollow needle.

16. An apparatus as in claim 14, further comprising a fluid supply vessel, said tube extending between said fluid supply vessel and said handpiece.

17. An apparatus as in claim 14, wherein said support is a rigid strip.

18. An apparatus as in claim 17, wherein said strip is on an exterior of said tube.

19. An apparatus as in claim 17, wherein said tube defines a lumen, said strip being within said lumen.

20. An apparatus as in claim 17, wherein said strip is embedded within said tube.

* * * * *